(12) United States Patent
Larsson

(10) Patent No.: US 10,115,298 B2
(45) Date of Patent: Oct. 30, 2018

(54) METHOD OF TREND ANALYSIS AND AUTOMATIC TUNING OF ALARM PARAMETERS

(71) Applicant: Aktiebolaget SKF, Gothenburg (SE)

(72) Inventor: Per-Erik Larsson, Lulea (SE)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/367,652

(22) Filed: Dec. 2, 2016

(65) Prior Publication Data

US 2018/0158314 A1    Jun. 7, 2018

(51) Int. Cl.
| | |
|---|---|
| G08B 31/00 | (2006.01) |
| G08B 29/26 | (2006.01) |
| G08B 29/18 | (2006.01) |
| G05B 23/02 | (2006.01) |
| G05B 23/00 | (2006.01) |
| G01N 19/08 | (2006.01) |
| G08B 29/00 | (2006.01) |
| G08B 29/04 | (2006.01) |
| G05B 19/4063 | (2006.01) |

(52) U.S. Cl.
CPC ............ *G08B 29/26* (2013.01); *G05B 23/00* (2013.01); *G05B 23/02* (2013.01); *G05B 23/0205* (2013.01); *G05B 23/0218* (2013.01); *G08B 29/186* (2013.01); *G08B 31/00* (2013.01); *G01N 19/08* (2013.01); *G05B 19/4063* (2013.01); *G05B 23/024* (2013.01); *G05B 23/0235* (2013.01); *G05B 23/0243* (2013.01); *G08B 29/00* (2013.01); *G08B 29/04* (2013.01)

(58) Field of Classification Search
CPC ........ G01N 19/08; G08B 29/00; G08B 29/04; G08B 31/00; G08B 29/185; G05B 23/00; G05B 23/02; G05B 23/0235; G05B 23/0205; G05B 23/0218; G05B 23/0243; G05B 23/022; G05B 23/023; G05B 23/024; G05B 19/4063; G05B 2219/50185
See application file for complete search history.

(56) References Cited

U.S. PATENT DOCUMENTS

| | | | |
|---|---|---|---|
| 6,681,633 B2 * | 1/2004 | Schultz | E21B 12/02 73/152.46 |
| 2012/0259583 A1* | 10/2012 | Noboa | G05B 15/02 702/179 |
| 2017/0090457 A1* | 3/2017 | Pandurangan | E21B 43/121 |

* cited by examiner

*Primary Examiner* — Benyam Haile
(74) *Attorney, Agent, or Firm* — Bryan Peckjian; SKF USA Inc. Patent Dept.

(57) ABSTRACT

A method of trend analysis and automatic tuning of alarm parameters for a machine is provided. The method includes obtaining condition related measurements of the machine, checking a Condition Indicator (CI) value with respect to a set threshold, calculating the number of times the value is above the threshold during the N last measurements, displaying the number of times the value is above the threshold during the N last measurements in a diagram, triggering the alarm if the value has been above the threshold more times than the alarm level during the N last measurements, comparing historical measurement data when each alarm triggered with defects recorded, correlating a relationship between the alarms triggered and the defects detected, counting the number of true positives, false negatives and false positives from the current measurement data, comparing the number of counted true positives, false negatives and false positives with the acceptable defined limits.

14 Claims, 3 Drawing Sheets

METHOD OF TREND ANALYSIS AND AUTOMATIC TUNING OF ALARM PARAMETERS

FIELD OF THE INVENTION

This invention relates to a method of trend analysis and automatic tuning. In particular, this invention relates to a method of trend analysis and automatic tuning of alarm parameters for a machine.

BACKGROUND OF THE INVENTION

In the field of condition monitoring a common problem is that the running conditions of a machine are constantly changing and consequently the measurement value of a condition indicator is changing as well. That makes it difficult to set appropriate alarm thresholds and the risk of false alarms is quite high. Today a lot of effort has been spent on creating robust condition indicators and using alarm hysteresis to avoid spurious alarms.

SUMMARY OF THE INVENTION

The basic inventive concept provides a method of trend analysis and tuning of alarm parameters for a machine.

A first aspect of the present invention provides a method comprising the steps of obtaining a series of condition related measurements of the machine, wherein the Condition Indicator (CI) value relates to a condition of the machine with respect to the defect, checking the Condition Indicator (CI) value with respect to a set threshold, calculating the number of times the Condition Indicator (CI) value is above the threshold during the N last measurements, displaying the number of times the Condition Indicator (CI) value is above the threshold during the N last measurements in a diagram with Date/Time on the x-axis and Number of Times on the y-axis, and triggering the alarm if the Condition Indicator (CI) value has been above the threshold more times than the alarm level during the N last measurements, obtaining the historical measurement data from the machine that is normally regularly recorded as above, which includes defects detected and when alarms were triggered, comparing the historical measurement data when each alarm triggered against current machine measurement data when each alarm triggered with the defects recorded, correlating a relationship between the alarms triggered and the defects detected, wherein a relationship is correlated if an alarm was recorded a set period of time in advance of the defect being detected, and wherein if a relationship exists between the alarm and the defect, then the alarm is defined as a true positive (TP) alarm, if a defect was detected, but no alarm was triggered, then the defect is defined as a false negative (FN), if an alarm was triggered without a defect being recorded, then the defect is defined as a false positive (FP), setting acceptable defined limits for true positives (TP), false negatives (FN) and false positives (FP) based on acceptable historical measurement data, counting the number of true positives (TPs), false negatives (FNs) and false positives (FPs) from the current measurement data, comparing the number of counted true positives (TPs), false negatives (FNs) and false positives (FPs) with the acceptable defined limits, wherein if the compared number of counted true positives (TPs), false negatives (FNs) and false positives (FPs) are within the acceptable defined limits, then tuning is complete, if the compared number of counted true positives (TPs), false negatives (FNs) and false positives (FPs) are not within the acceptable defined limits then the tuning is incomplete, and wherein tuning the calculation of the Condition Indicators (CIs), the threshold, the M and the N is automatically carried out until the acceptable defined limits are reached.

In a second aspect of the present invention the method provides during the step of obtaining a series of condition related measurements, each measurement contains a time series of data points that creates a time waveform.

In a third aspect of the invention the method includes performing a signal analysis on the time waveform (FFT) to create a spectrum.

In yet another aspect of the present invention the method determines a defect associated with the condition related measurements by spectral peaks disposed on the time waveform.

In yet another aspect of the present invention the method provides identifying the spectral peaks relevant to a particular defect to be analysed.

In yet another aspect of the present invention the method includes calculating the Condition Indicator (CI) value from the identified spectral peaks.

In yet another aspect of the present invention the method provides multiple Condition Indicator CI values, each one designed to detect a defect and calculated from each measurement.

In yet another aspect of the present invention the series of condition related measurements of the mechanism is at least one of a vibration and a temperature.

In yet another aspect of the present invention each measurement contains a time series of 1024 to 16384 data points.

In a final aspect of the present invention the method provides if the number of false positives (FPs) exceeds the acceptable defined limits then increase at least one of the threshold the M and the N, if the number of false negatives (FNs) exceeds the acceptable defined limits then decrease at least one of the threshold the M and the N, and wherein the step is repeated until the alarm parameters are tuned.

These and other advantages of the invention will be further understood and appreciated by those skilled in the art by reference to the following written specification, claims and appended drawings.

BRIEF DESCRIPTION OF THE SEVERAL VIEWS OF THE DRAWINGS

The invention will now be described, by way of example, with reference to the accompanying drawings, in which.

DETAILED DESCRIPTION OF THE INVENTION

Figure 1:
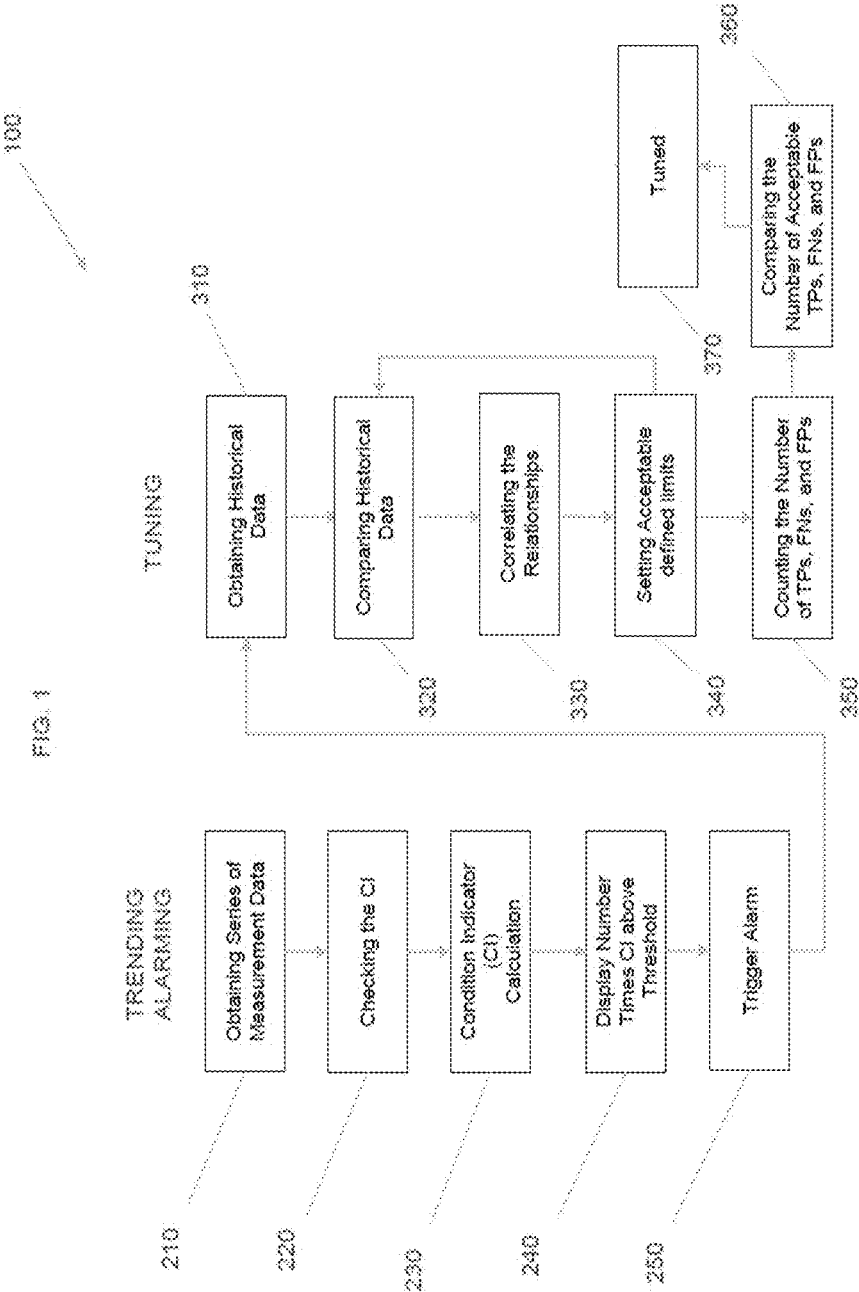
FIG. 1 is a flow diagram of a method trend analysis and automatic tuning according to the present invention.

The following detailed description refers to the accompanying drawings. Wherever possible, the same reference numbers are used in the drawings and the following description refers to the same or similar parts. While several exemplary embodiments and features of the present disclosure are described herein, modifications, adaptations, and other implementations are possible, without departing from the spirit and scope of the present disclosure. Accordingly, the following detailed description does not limit the present disclosure. Instead, the proper scope of the disclosure is defined by the appended claims.

FIG. 1 is a flow diagram illustrating a method 100 of trend analysis 200 and tuning 300 of alarm parameters for a machine.

Here, the invention contemplates a machine where a number of condition related measurements are done. One such measurement, e.g. a vibration measurement can be considered for discussion purposes, but the measurement can be any number of condition related measurements including temperature, force, dynamic pressure, etc.

The method 100 of trend analysis 200 provides a step 210 of a obtaining series of condition related measurements of the machine. Each measurement can contain a time series of 1024 to 16384 data points, which represents a time waveform. The method includes performing a signal analysis on that waveform called FFT, which creates a spectrum.

From there, spectrum peaks relevant to a particular defect are picked and used to calculate a Condition Indicator (CI) value that reflects the condition of the machine with respect to that defect. It should be noted that several CI values, each one designed to detect a defect, can be calculated from each measurement. As such, there is one CI value for each measurement.

In a next step 220 the Condition Indicator (CI) value is checked with respect to a set threshold.

The system then calculates the number of times the CI value is above the threshold during the N last measurements in step 230.

This number of times is then displayed in a diagram with Date/Time on the x-axis and Number of Times on the y-axis in step 240.

In step 250, if the Condition Indicator (CI) value has been above the threshold more times than the alarm level during the N last measurements an alarm is triggered.

The method 100 of tuning 300 provides a step 310 of obtaining historical measurement data from the machine that is normally regularly recorded by a technician. The historical measurement data includes defects detected and when alarms were triggered as per previous steps 210-250. As an example, a wind park and defects in the main bearing of each wind turbine can be chosen.

Then in step 320, we can compare the historical measurement data when each alarm triggered against current machine measurement data when each alarm triggered with the defects detected and recorded.

Step 330 provides correlating a relationship between the alarms triggered and the defects detected. A relationship is correlated if an alarm was recorded a set period of time in advance of the defect being detected. As such, if we see a correlation between the alarm and the defect, i.e. an alarm was registered a month before the defect was detected, then the alarm is defined as a true positive (TP) alarm. GOOD! If a defect was detected, but no alarm was triggered, then the defect is defined as a false negative (FN). BAD! Finally, if an alarm was triggered without a defect being recorded, then the defect is defined as a false positive (FP). BAD!

Step 340 provides setting acceptable defined limits for true positives (TP), false negatives (FN) and false positives (FP) based on acceptable historical measurement data.

Step 350 provides counting the number of true positives (TPs), false negatives (FNs) and false positives (FPs) from the current measurement data and in step 360 comparing the number of counted true positives (TPs), false negatives (FNs) and false positives (FPs) with what has been defined as acceptable limits. For example for a wind park of 100 wind turbines it could be acceptable to trigger maximum 10 FPs and 2 FNs in one year. However, in order to feel safe, we should have experienced at least 10 TPs during the same period of time.

Consequently, if the compared number of counted true positives (TPs), false negatives (FNs) and false positives (FPs) are within the acceptable defined limits, then tuning is complete as per step 370.

However, if the compared number of counted true positives (TPs), false negatives (FNs) and false positives (FPs) are not within the acceptable defined limits then the tuning is incomplete.

Therefore, tuning the calculation of the Condition Indicators (CIs), the threshold, the M and the N is automatically carried out until the acceptable defined limits are reached. This is done by going back to method step 340 setting/adjusting the acceptable defined limits until the tuning is complete.

Figure 2:
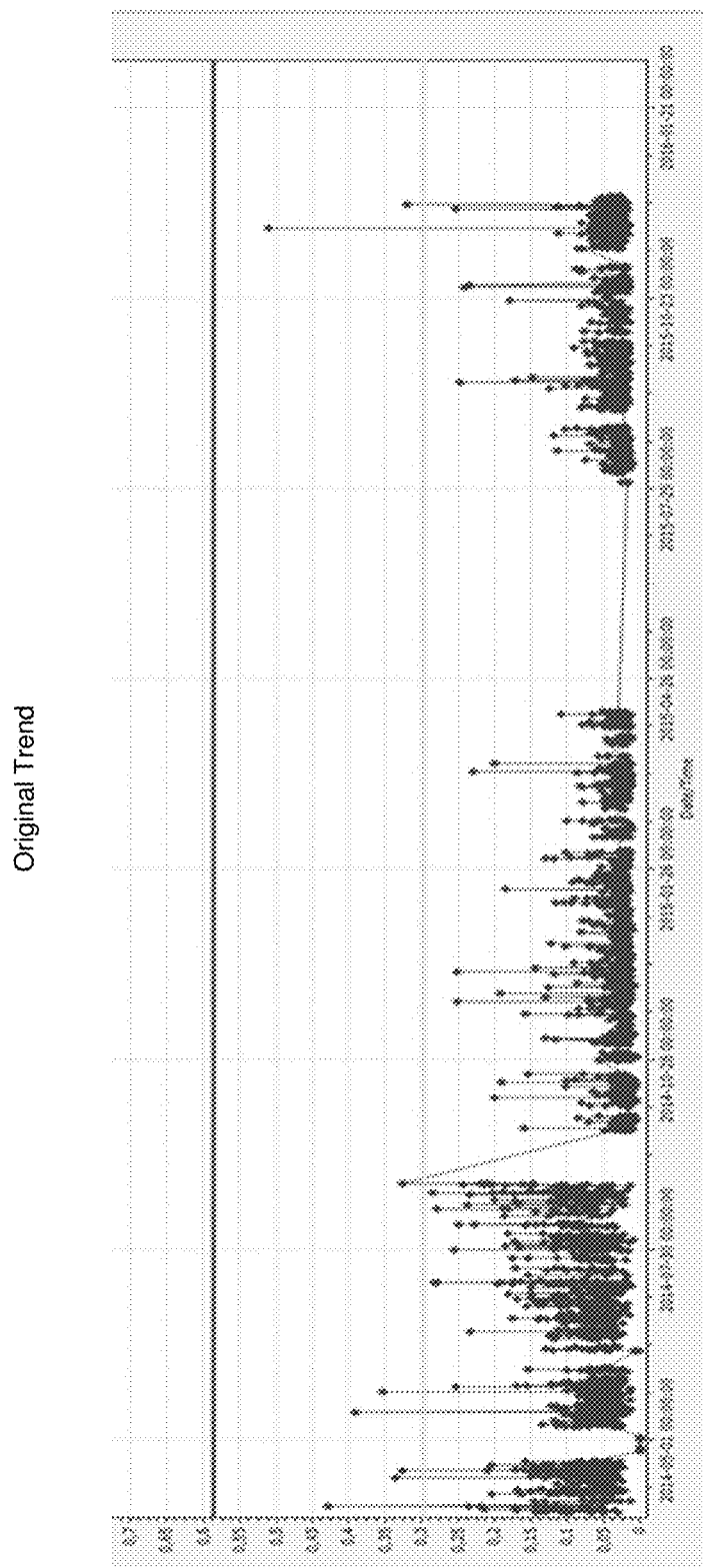
FIG. 2 is a graph of an example of original trends coming from a defect bearing with an outer race spall having defects difficult to detect according to the prior art.

FIG. 2 illustrates trends coming from a defective bearing with an outer race spall.

Figure 3:
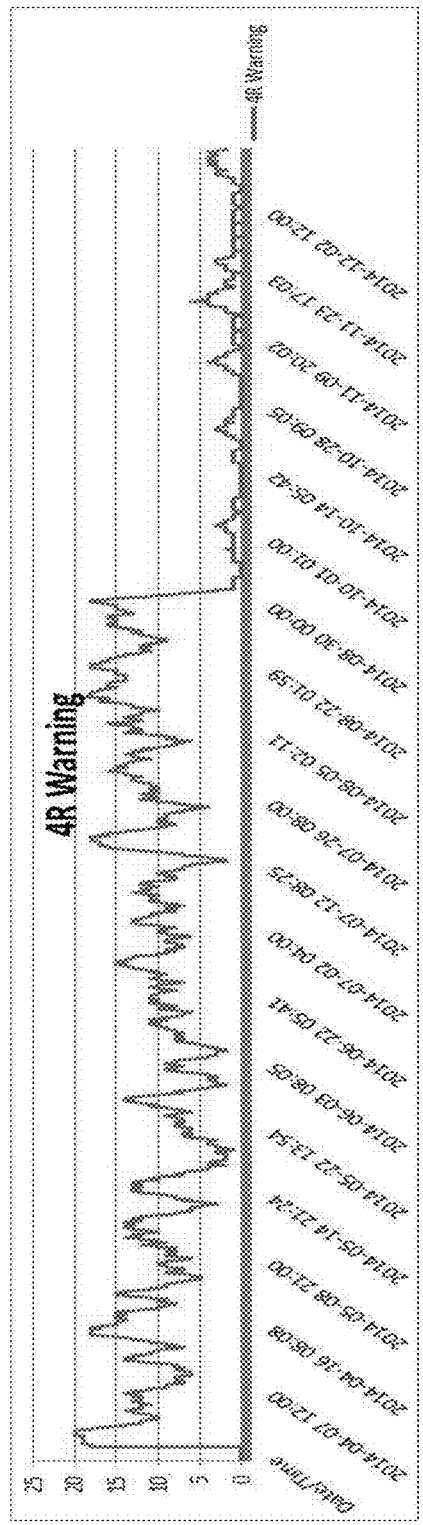
FIG. 3 is a graph of an example of new trends coming from a defect where the new trends are stable according to the present invention.

The defect is difficult to trend, but is shown clearly in the new trend illustrated in FIG. 3.

After the bearing was replaced (2014 Sep. 15) the original trend of FIG. 2 shows some unstable behaviour however the new trend of FIG. 3 is very stable.

The invention claimed is:

1. A method of trend analysis of alarm parameters for a machine, the method comprising:
    obtaining a series of condition related measurements of the machine, each of the condition related measurements comprises a time series of data points creating a time waveform,
    performing a signal analysis on the time waveform to create a spectrum,
    utilizing a peak of the spectrum, the peak being relevant to a defect, to calculate a Condition Indicator (CI) value that relates to a condition of the machine with respect to the defect,
    checking the Condition Indicator (CI) value with respect to a set threshold,
    calculating the number of times the Condition Indicator (CI) value is above the set threshold during N last measurements,
    displaying the number of times the Condition Indicator (CI) value is above the set threshold during the N last measurements in a diagram with Date/Time on the x-axis and Number of Times on the y-axis, and
    triggering the alarm if the Condition Indicator (CI) value has been above the set threshold more times than the alarm level during the N last measurements,
    automatically tuning of the alarm parameters, including the calculation of the Condition Indicator (CI), for the machine by repeatedly:
        increasing the set threshold if a number of false positives (FPs) exceeds a first defined limit, the false positives include when an alarm is triggered without a defect being recorded, and
        decreasing the set threshold if a number of false negatives (FNs) exceeds a second defined limit, the false negatives include when a defect is detected without an alarm being triggered.

2. The method of trend analysis of alarm parameters for a machine according to claim 1, further comprising determining the defect associated with the condition related measurements by spectral peaks disposed on the time waveform.

3. The method of trend analysis of alarm parameters for a machine according to claim 2, further comprising identifying the spectral peaks relevant to a particular defect to be analyzed.

4. The method of trend analysis of alarm parameters for a machine according to claim 3, further comprising calculating the Condition Indicator (CI) value from the identified spectral peaks.

5. The method of trend analysis of alarm parameters for a machine according to claim 1, further comprising multiple Condition Indicator CI values, each one designed to detect a defect and calculated from each measurement.

6. The method of trend analysis of alarm parameters for a machine according to claim 1, wherein the series of condition related measurements of the mechanism is at least one of a vibration and a temperature.

7. The method of trend analysis of alarm parameters for a machine according to claim 1, wherein each measurement contains a time series of 1024 to 16384 data points.

8. A method of automatic tuning of alarm parameters for a machine, the method comprising:
   obtaining a series of condition related measurements of the machine, each of the condition related measurements comprises a time series of data points creating a time waveform,
   performing a signal analysis on the time waveform to create a spectrum,
   utilizing a peak of the spectrum, the peak being relevant to a defect, to calculate a Condition Indicator (CI) value that relates to a condition of the machine with respect to the defect,
   obtaining historical measurement data from the machine that is normally regularly recorded, which includes defects detected and when alarms were triggered,
   comparing the historical measurement data when each alarm triggered against current machine measurement data when each alarm triggered with the defects recorded,
   correlating a relationship between the alarms triggered and the defects detected, wherein a relationship is correlated if an alarm was recorded a set period of time in advance of the defect being detected, and
   wherein if a relationship exists between the alarm and the defect, then the alarm is defined as a true positive (TP) alarm, if a defect was detected, but no alarm was triggered, then the defect is defined as a false negative (FN), and if an alarm was triggered without a defect being recorded, then the defect is defined as a false positive (FP),
   setting defined limits for true positives (TP), false negatives (FN) and false positives (FP) based on historical measurement data,
   counting a number of true positives (TPs), a number of false negatives (FNs) and a number of false positives (FPs) from the current measurement data,
   automatically tuning of the alarm parameters, including the calculation of the Condition Indicator (CI), for the machine by repeatedly:
      increasing a first set threshold if the number of false positives (FPs) exceeds a first defined limit, the false positives include when an alarm is triggered without a defect being recorded, and
      decreasing the set threshold if a number of false positives (FPs) exceeds a first defined limit, the false negatives include when a defect is detected without an alarm being triggered, and
   wherein if the number of true positives (TPs), false negatives (FNs) and false positives (FPs) are within the defined limits, then the automatic tuning is complete, and
   wherein if the number of true positives (TPs), false negatives (FNs) and false positives (FPs) are not within the defined limits then the tuning is incomplete.

9. The method of trend analysis of alarm parameters for a machine according to claim 8, further comprising determining a defect associated with the condition related measurements by spectral peaks disposed on the time waveform.

10. The method of trend analysis of alarm parameters for a machine according to claim 9, further comprising identifying the spectral peaks relevant to a particular defect to be analyzed.

11. The method of trend analysis of alarm parameters for a machine according to claim 10, further comprising calculating the Condition Indicator (CI) value from the identified spectral peaks.

12. The method of trend analysis of alarm parameters for a machine according to claim 8, further comprising multiple Condition Indicator CI values, each one designed to detect a defect and calculated from each measurement.

13. The method of trend analysis of alarm parameters for a machine according to claim 8, wherein the series of condition related measurements of the mechanism is at least one of a vibration and a temperature.

14. The method of trend analysis of alarm parameters for a machine according to claim 8, wherein each measurement contains a time series of 1024 to 16384 data points.

* * * * *